United States Patent
Stein et al.

(10) Patent No.: US 6,406,735 B2
(45) Date of Patent: *Jun. 18, 2002

(54) PROCESS FOR PREPARING A FINELY DIVIDED PULVEROUS CAROTENOID RETINOID OR NATURAL COLOURANT PREPARATION

(75) Inventors: Hermann Stein, Liestal; Klaus Viardot, Riehen; Bin Yang, Möhlin, all of (CH)

(73) Assignee: Roche Vitamins Inc., Parsippany, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/255,010

(22) Filed: Feb. 22, 1999

(30) Foreign Application Priority Data

Feb. 23, 1998 (EP) ............................................... 98103113

(51) Int. Cl.⁷ .................................................. A23L 1/27
(52) U.S. Cl. ........................ 426/540; 426/519; 426/520; 424/451; 424/456; 516/77
(58) Field of Search ..................... 426/73, 540, 519, 426/520; 516/77; 424/451, 456, 401, 489

(56) References Cited

U.S. PATENT DOCUMENTS

| | | | |
|---|---|---|---|
| 2,861,891 A | * | 11/1958 | Bauernfeind et al. .......... 99/148 |
| 3,110,598 A | * | 11/1963 | Müller et al. ................... 99/148 |
| 3,316,101 A | * | 4/1967 | Borenstein et al. ............ 99/148 |
| 3,655,406 A | * | 4/1972 | Klaui .......................... 99/148 |
| 3,790,688 A | | 2/1974 | Walter, Jr. et al. |
| 3,998,753 A | | 12/1976 | Antoshkiw et al. |
| 4,522,743 A | | 6/1985 | Horn et al. |
| 4,726,955 A | | 2/1988 | Horn et al. |
| 4,844,934 A | | 7/1989 | Lueddecke et al. |
| 5,364,563 A | | 11/1994 | Cathrein et al. |
| 5,895,659 A | * | 4/1999 | Luddecke et al. .......... 424/442 |
| 6,261,598 B1 | * | 7/2001 | Runge et al. ................ 424/456 |

FOREIGN PATENT DOCUMENTS

| | | |
|---|---|---|
| DE | 1 211 911 | 3/1966 |
| EP | 0 065 193 B1 | 5/1982 |

* cited by examiner

*Primary Examiner*—Nina Bhat
(74) *Attorney, Agent, or Firm*—Bryan Cave LLP

(57) ABSTRACT

A process for the preparation of a pulverous preparation having a finely divided carotenoid, retinoid or natural colorant is provided, which process comprises the steps of:

a) forming a suspension of the active ingredient in a water-immiscible organic solvent optionally containing an antioxidant and/or an oil;

b) feeding the suspension of step a) to a heat exchanger;

c) heating the suspension to 100–250° C., whereby the residence time in the heat exchanger is less than 5 sec to provide a solution;

d) rapidly mixing the solution of step c) with an aqueous solution of a swellable colloid and optionally a stabilizer such that the resulting mixture is at a temperature in the range of 20–100° C.;

e) removing the organic solvent; and f) converting the dispersion of step e) into a pulverous preparation;

where steps b) to f) are carried out continuously and in sequence.

18 Claims, 1 Drawing Sheet

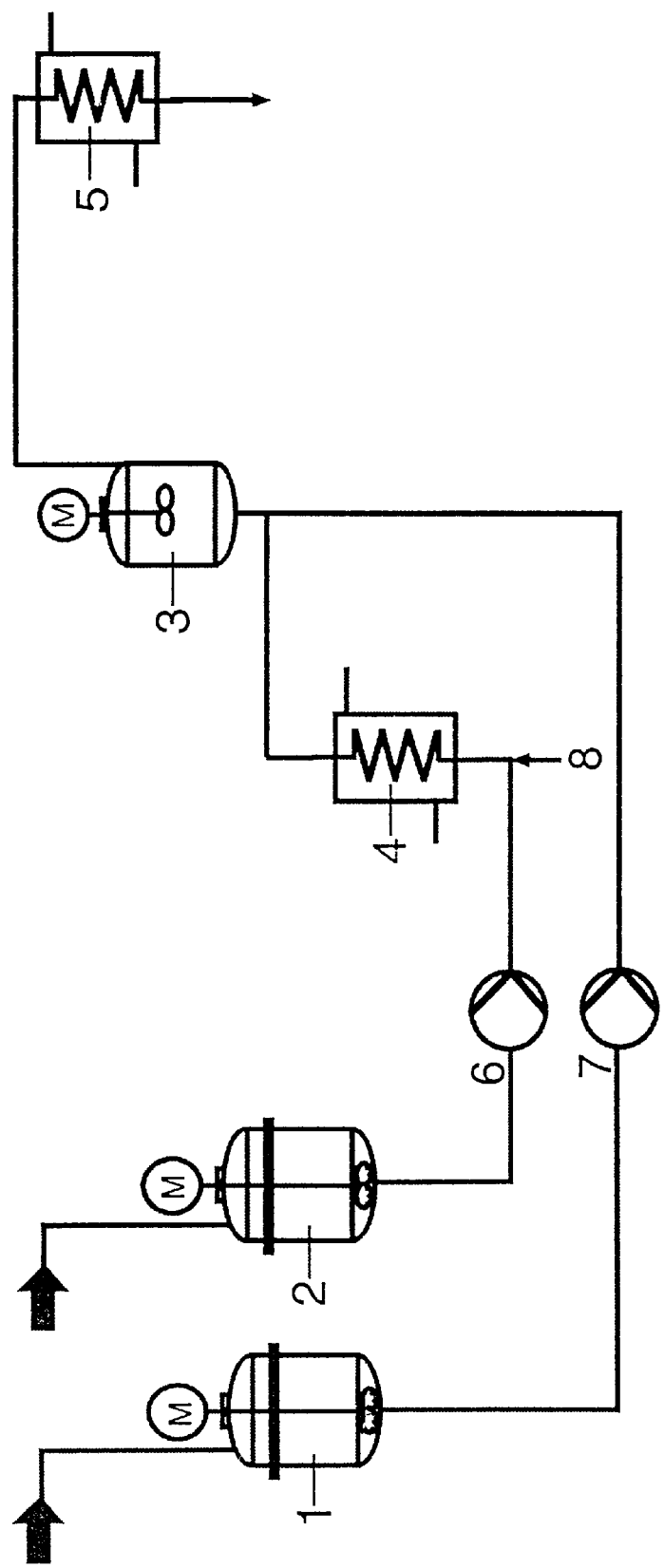

PROCESS FOR PREPARING A FINELY DIVIDED PULVEROUS CAROTENOID RETINOID OR NATURAL COLOURANT PREPARATION

FIELD OF THE INVENTION

The present invention relates to a continuous process for converting carotenoids, retinoids or natural colourants into finely divided pulverous forms which are particularly useful for coloring foodstuff and animal feeds.

BACKGROUND OF THE INVENTION

Various processes have been described to prepare a powder containing the active ingredients with a crystallite size less than 1 micron. Most of the processes are well suited to batch processing applications.

For example, U.S. Pat. No. 3,998,753 describes a batch process for the preparation of a water dispersible carotenoid-containing powder, wherein the carotenoid powder has a particle size of less than 1 micron, which process comprises (a) forming a solution of a carotenoid and an antioxidant in a volatile solvent, said solvent being selected from the group consisting of halogenated aliphatic hydrocarbons such as chloroform, carbon tetra-chloride and methylene chloride; (b) forming an aqueous solution of sodium lauryl sulfate, a water soluble carrier composition such as e.g. gelatin, a preservative and a stabilizer, and adjusting said solution to a pH of about 10 to 11 and (c) forming an emulsion of the solutions of steps (a) and (b) by mixing at a high speed and high shear; removing the organic solvent and spray drying the resulting emulsion to obtain a carotenoid powder.

In the European Patent Publication EP-0065 193 B1 or the corresponding U.S. Pat. No. 4,522,743 a continuous process for the preparation of finely divided carotenoid powders is described, in which the carotenoid has a particle size essentially below 0.5 microns. The carotenoid is dissolved in a volatile, water miscible organic solvent within less than 10 sec. at 50–200° C. The carotenoid is immediately precipitated in colloidally dispersed form from the resulting molecularly dispersed solution by rapid mixing with an aqueous solution of a swellable colloid at 0–50° C. The preparation of the carotenoid solution and the precipitation of the carotenoid are effected continuously in two mixing chambers. The resulting dispersion is freed of solvent and the dispersing medium in a conventional manner.

However, for economical and ecological reasons this process has the disadvantage that a large amount of solvent must be used.

SUMMARY OF THE INVENTION

It is an object of the present invention to provide a process that overcomes the aforesaid drawback while converting the active ingredient into finely divided pulverous form.

The present invention is a process for preparing a pulverous preparation of a finely divided carotenoid, retinoid or natural colourant, which process comprises the steps of:

a) forming a suspension having an active ingredient which is taken from the group of carotenoids, retinoid and natural colourants, in a water-immiscible organic solvent optionally containing an antioxidant and/or an oil;

b) feeding the suspension of step a) to a heat exchanger;

c) heating said suspension to 100–250° C., whereby the residence time in the heat exchanger is less than 5 sec to provide a solution;

d) rapidly mixing the solution of step c) with an aqueous solution of a swellable colloid such that the resulting mixture is at a temperature in the range of 20–100° C.;

e) removing the organic solvent to provide a dispersion; and f) converting the dispersion of step e) into a pulverous preparation;

where steps b) to f) are carried out continuously and in sequence.

BRIEF DESCRIPTION OF THE FIGURE

FIG. 1 depicts a flow chart of the continuous process of the present invention.

DETAILED DESCRIPTION OF THE INVENTION

It has now been found that it is possible to provide a pulverous preparation wherein the active ingredient is finely divided by using a water-immiscible organic solvent in a continuous process.

The term "finely divided" denotes in the scope of the present invention a particle size of less than 1.5 micron, preferably less than 1 micron, more preferably less than 0.4 micron.

The term "active ingredient" denotes in the scope of the present invention carotenoids, retinoids or natural colourants.

Carotenoids for the purpose of the present invention in particular include beta-carotene, beta-apo-4'-carotenal, beta-apo-8'-carotenal, beta-apo-12'-carotenal, beta-apo-8'-carotenic acid, astaxanthin, canthaxanthin, zeaxanthin cryptoxanthin, citranaxanthin, lutein, lycopene, torularodinaldehyde, torularodin-ethylester, neurosporaxanthin-ethylester, zeta-carotene or dehydroplectaniaxanthin. Also included are carotenoids of natural sources. Preferred are beta-carotene, astaxanthin, canthaxanthin, beta-apo-8'-carotenal and lycopene; more preferred is beta-carotene.

Natural colourants for the purpose of the present invention in particular include curcumine, cochineal, carmine, annatto and mixtures thereof.

Preferably the process of the invention is carried out using carotenoids.

The temperature of step b) is preferably 120–180° C., more preferably 140–170° C. and the temperature of step c) is preferably 50–80° C.

The residence time in the heat exchanger is preferably 0.5–4 sec, more preferably 1–3 sec.

The term "water-immiscible organic solvent" denotes in the scope of the present invention an organic solvent having a solubility in water of less than 10% under atmospheric pressure. Suitable water-immiscible organic solvents for carrying out the continuous process according to the invention are halogenated aliphatic hydrocarbons such as e.g. chloroform, carbon tetrachloride and methylene chloride, water-immiscible esters such as e.g. carbonic acid dimethylester (dimethyl carbonate), formic acid ethylester (ethyl formate) methyl-, ethyl-, or isopropylacetate; or water-immiscible ethers such as e.g. methyl-tert. butylether and the like. Preferred are dimethyl carbonate, ethyl formate, ethyl-, or isopropylacetate, methyl-tert. butylether.

The term "swellable colloids" denotes in the scope of the present invention gelatin, carbohydrates such as e.g. starch or starch derivatives, dextrin, pectin, gum arabic, octenylbutanedioate amylodextrin (CAPSUL™), milk protein such as e.g. casein and vegetable protein as well as mixtures thereof. Preferred are fish gelatin or starch derivatives.

The process can be optionally carried out such that in forming the suspension in accordance with step a) an antioxidant and/or an oil is present in the water-immiscible organic solvent.

To increase the stability of the carotenoid it is advantageous to add an antioxidant being selected from the group consisting of ascorbic acid, ascorbylpalmitate, dl-alpha tocopherol, mixed tocopherols, lecithine, butylhydroxytoluol, butyl-4-methoxyphenol and combinations of these compounds.

The antioxidant can be added either to the matrix solution or to the carotenoid solution or to both solutions. For example, an antioxidant can be present in the water-immiscible organic solvent during the formation of the suspension in accordance with step a). A preferred antioxidant for the carotenoid solution is dl-alpha tocopherol and for the aqueous phase solution it is ascorbyl palmitate.

It may be further advantageous to dissolve an oil in the carotenoid suspension, preferably corn oil. An oil can be present in the water-immiscible organic solvent during the formation of the suspension in accordance with step a), for instance.

The process can optionally be carried out such that the aqueous solution of a swellable colloid in step d) can optionally include a stabilizer.

Steps b) to f) are carried out continuously. Performing steps b) to f) of the present process in a batch-wise manner is not typically successful. Step a) can be carried out batchwise.

Reference is now made to the accompanying drawing FIG. 1 where a flow chart suitable for carrying out the process in accordance with the instant invention is diagrammatically illustrated.

An aqueous matrix containing a swellable colloid and optionally a stabilizer is prepared in chamber 1.

A suspension of a carotenoid in the selected solvent is prepared in chamber 2. The suspension may further contain an antioxidant and an oil.

The carotenoid suspension is fed continuously by pump 6 to heat exchanger 4. The flow rate is adjusted according to the desired residence time which is necessary to dissolve the carotenoid in the solvent at a given temperature. In heat exchanger 4 the carotenoid suspension is heated to 100 to 250° C., preferably to 120 to 180° C., more preferably to 140 to 170° C., and the carotene is solubilized. The heating can be done either indirectly through heat exchanger 4 or directly by mixing with steam 8 which flows in-line from an outside steam source (not shown). For the purposes of the present invention, the heat exchanger can provide indirect heating or the heat exchanger, when operatively connected with the outside source for steam 8, can refer to a chamber in which heat is supplied by the direct addition of steam 8. The residence time in the heat exchanger is less than 5 sec, preferably 1 to 3 sec.

The matrix solution of chamber 1 is fed by pump 7 to chamber 3. The flow rate depends on the suspension flow rate and the required emulsion composition. In chamber 3 the carotenoid suspension and the matrix are mixed and emulsified by using a rotor stator homogenizer to the desired particle size of the inner phase of approx. 150–400 nm. As a result of the mixing the temperature is lowered to the range 20 to 100° C.

The dispersion obtained passes to a second heat exchanger 5 whereby the dispersion is cooled. The pressure is released to atmospheric pressure by pressure control.

The solvent is removed using conventional methods e.g. by evaporation. A pulverous composition can be isolated from the resulting dispersion by conventional methods, for example, by spray drying or by using powder catch technique.

Using this invention it is possible to manufacture powders which cover a very wide range of color.

The manner in which the process of the invention may readily be carried out is illustrated by the following examples. The color intensity was measured in an aqueous dispersion containing 5 ppm carotenoid and given by the calculated extinction of 1% solution in a 1 cm cuvette (E1/1-value). The average particle size has been measured by Coulter Particle Analyzer N4S. The carotenoid content was measured by UV-spectroscopy.

EXAMPLE 1

Solvent: ethyl acetate; indirect heat transfer.

The aqueous matrix was prepared in chamber 1. Thus, 1.0 kg of ascorbyl palmitate was dispersed in 27.8 kg of water at 60° C. The pH-value of this dispersion was adjusted with NaOH (20%) to 7.2–7.6. Then 3.4 kg of fish gelatin and 7.2 kg of sucrose were added. The resulting mixture was stirred until a viscous, clear solution was obtained.

0.75 kg of all-trans-β-carotene cryst. were dispersed in chamber 2 in a mixture of 90 g of dl-α-tocopherol, 330 g of corn oil and 7.5 kg of ethyl acetate.

The carotene suspension was fed continuously at a rate of 6 kg/h via pump 6 to the heat exchanger 4, heated to 160° C. and the carotene was solubilized. The residence time in the heat exchanger was 4 sec.

The matrix solution of chamber 1 was fed via pump 7 with a flow rate of 9.2 kg/h to chamber 3 and mixed with the carotene solution.

The resulting emulsion was cooled in a second heat exchanger 5 to 60° C. and the pressure was released to atmospheric pressure.

Ethyl acetate was removed in a thin film evaporator. The resulting emulsion showed a particle size of the inner phase of 225 nm and was spray dried. A powder with the following specifications was obtained: 11.6% carotene content, E 1/1=1015, λ max. 440–460 nm. The powder was well soluble in cold water with an intense red coloration.

EXAMPLE 2

Solvent: isopropyl acetate; direct heat transfer (steam).

1.25 kg of Ascorbyl palmitate was dispersed in 30.9 kg water at 60° C. according to Example 1. The pH-value of this dispersion was adjusted with NaOH (20%) to 7.2–7.6. Then 5.1 kg of fish gelatin and 7.1 kg of sucrose were added. The resulting mixture was stirred until a viscous, clear solution was obtained.

0.75 kg of Canthaxanthin cryst. were dispersed in chamber 2 in a mixture of 0.10 kg of dl-α-tocopherol, 0.36 kg of corn oil and 6.25 kg of isopropyl acetate.

The canthaxanthin suspension was fed continuously at a rate of 6 kg/h via pump 6 to the mixing chamber where the temperature was raised by injection of steam to 170° C. Then, the hot canthaxanthin dispersion passed within 2 sec. through the heat exchanger 4 where the canthaxanthin was solubilized.

The matrix solution of chamber 1 was fed via pump 7 with a flow rate of 0.1 kg/h to chamber 3 and mixed with the canthaxanthin solution.

The resulting emulsion is cooled in heat exchanger 5 to 60° C. and the pressure was released to atmospheric pressure.

Isopropyl acetate was removed in a thin film evaporator. The resulting emulsion showed a particle size of the inner phase of 213 nm and was spray dried. A powder with the following specifications was obtained: 12.3% canthaxanthin content, E 1/1=905, λ max, 470–485 nm. The powder was well soluble in cold water with an intense cherry-red coloration.

EXAMPLE 3

Solvent: isopropyl acetate; direct heat transfer (steam).

10.3 kg of Fish gelatin, 20.6 kg of sugar and 2.78 kg of ascorbyl palmitate were dissolved in 27.56 kg of water in chamber 1. The pH-value of this matrix was adjusted with NaOH (20%) to 7.2–7.6.

6.68 kg of β-Carotene, 0.84 kg of dl-α-tocopherol and 3.34 kg of corn oil were dispersed in 33.4 kg of isopropyl acetate in chamber 2.

The β-carotene suspension was fed by pump 6 with a flow rate of 25 kg/h to heat exchanger 4 where it was mixed with steam to reach an outlet temperature of 160° C. The residence time in the heat exchanger 4 was 1.0 sec. The matrix was pumped by pump 7 with a flow rate of 34.5 kg/h to chamber 3 where the solved β-carotene was mixed with the matrix and emulsified in it. The emulsion was cooled down to 60° C. in heat exchanger 5.

Isopropyl acetate was removed from the emulsion by using a vertical evaporator. The resulting emulsion showed a particle size of the inner phase of 220 nm and was spray dried.

The final product had a β-carotene content of 11.3%; E1/1: 1159, λ max. 440–460 nm. The powder was well soluble in water. The solution had a very intensive yellow color.

EXAMPLE 4

Solvent: isopropyl acetate; direct heat transfer (steam).

9.25 kg of Fish gelatin, 18.5 kg of sugar and 2.5 kg of ascorbyl palmitate were dissolved in 30.25 kg of water in chamber 1. The pH-value of this matrix was adjusted with NaOH (20%) to 7.2–7.6.

6.0 kg of β-Carotene, 0.75 kg of dl-α-tocopherol and 3.0 kg of corn oil were dispersed in 30.0 kg of isopropyl acetate in chamber 2.

The β-carotene suspension was fed by pump 6 with a flow rate of 20 kg/h to the heat exchanger 4 where it was mixed with steam to reach an outlet temperature of 158° C. The residence time in the heat exchanger 4 was 1.3 sec. The matrix was pumped by pump 7 with a flow rate of 30.4 kg/h to chamber 3 where the solved β-carotene was mixed with the matrix and emulsified in it. The emulsion is cooled down to 60° C. in heat exchanger 5.

Isopropyl acetate was removed from the emulsion by using a vertical evaporator. The resulting emulsion showed a particle size of the inner phase of 240 nm and was spray dried.

The final product has a β-carotene content of 11.2%, E1/1:795, λ max. 440–460 nm. The powder was well soluble in water, the solution has a very intensive red color.

EXAMPLE 5

Solvent: methylene chloride; direct heat transfer (steam).

9.25 kg Fish Gelatin, 18.5 kg of sugar and 2.5 kg of Ascorbyl palmitate were dissolved in 30.25 kg of water in chamber 1. The pH-value of this matrix was adjusted with NaOH (20%) to 7.2–7.6.

6.0 kg of β-Carotene, 0.75 of kg dl-α-tocopherol and 3.0 kg of corn oil were dispersed in 30.0 kg of methylene chloride in chamber 2.

The β-carotene suspension was fed by pump 6 with a flow rate of 20 kg/h to the heat exchanger 4 where it was mixed with steam to reach an outlet temperature of 145° C. The residence time in the heat exchanger 4 was 1.3 sec. The matrix was pumped by pump 7 with a flow rate of 30.4 kg/h to the chamber 3 where the solved β-carotene was mixed with the matrix and emulsified in it. The emulsion was cooled down to 35° C. in heat exchanger 5.

Methylene chloride was removed from the emulsion by using a vertical evaporator. The resulting emulsion showed a particle size of the inner phase of 196 nm and was spray dried.

The final product has a β-carotene content of 9.9%, E1/1: 1120, $\lambda_{max}$: 440–460 nm. The powder was well soluble in water, the solution has a very intensive yellow color.

The above examples are illustrative and not limitative of the present invention.

What is claimed is:

1. A process for preparing a pulverous preparation having a finely divided carotenoid, retinoid or natural colourant, which process comprises the following steps:
    a) forming a suspension comprising an active ingredient selected from the
        group consisting of carotenoids, retinoids and natural colorants in a water-immiscible organic solvent selected from the group consisting of dimethyl carbonate, ethyl formate, ethylacetate, isopropylacetate, methyltert, butylether and methylene chloride and an oil that is present in the suspension in a maximum ratio of oil:active ingredient of 0.5:1;
    b) feeding the suspension to a heat exchanger;
    c) heating the suspension in the heat exchanger to 100–250° C., whereby the
        residence time is less than 5 seconds, to provide a solution;
    d) mixing the solution of step c) with an aqueous solution comprising a
        swellable colloid such that the resulting mixture is at a temperature in the range of 20–100° C.;
    e) removing the water-immiscible organic solvent from the mixture to
        provide a dispersion; and
    f) converting the dispersion into a pulverous preparation; where steps
        b) to f) are carried out continuously and in sequence.

2. The process according to claim 1, wherein the finely divided carotenoid, retinoid or natural colourant of the preparation has a particle size of less than 1.0 micron.

3. The process according to claim 1, wherein the finely divided carotenoid, retinoid or natural colourant of the preparation has a particle size of less than 0.4 micron.

4. The process according to claim 1, wherein the temperature of step c) is from 120 to 180° C., and the temperature of step d) is from 50 to 80° C.

5. The process according to claim 4, wherein the temperature of step c) is from 140 to 170° C.

6. The process according to claim 1, wherein the residence time in the heat exchanger is from 0.5 to 4 sec.

7. The process according to claim 1, wherein the residence time in the heat exchanger is from 1 to 3 sec.

8. The process according to claim 1, wherein the active ingredient is a carotenoid.

9. The process according to claim 8, wherein the carotenoid is selected from the group consisting of beta-carotene, beta-apo-4'-carotenal, beta-apo-8'-carotenal, beta-apo-12'-carotenal, beta-apo-8'-carotenic acid, astaxanthin, canthaxanthin, zeaxanthin cryptoxanthin, citranaxanthin, lutein, lycopene, torularodin-aldehyde, torularodin-ethylester, neurosporaxanthin-ethylester, zeta-carotene and dehydroplectaniaxanthin.

10. The process according to claim 1, wherein the swellable colloid is selected from the group consisting of gelatin, starch, starch derivatives, dextrin, pectin, gum arabic, octenylbutanedioate amylodextrin, milk protein, vegetable protein and mixtures thereof.

11. The process according to claim 1, wherein the suspension of the active ingredient is heated in accordance with step c) by the heat exchanger.

12. The process according to claim 1, wherein the suspension of the active ingredient is heated in accordance with step c) by mixing the suspension with steam.

13. The process according to claim 1, wherein the pulverous preparation is converted from the dispersion in accordance with step f) by spray drying or powder catch technique.

14. The process according to claim 1, wherein the suspension of step a) further comprises an antioxidant.

15. The process according to claim 1, wherein the antioxidant is selected from the group consisting of ascorbic acid, ascorbylpalmitate, dl-alpha tocopherol, mixed tocopherols, lecithine, butylhydroxytoluol, butyl-4-methoxy-phenol and combinations of these compounds.

16. The process according to claim 1, wherein the suspension of step a) comprises an oil:active ingredient ratio of from 0.44:1 to 0.5:1.

17. The process according to claim 1, wherein the aqueous solution further comprises an antioxidant.

18. A pulverous preparation prepared by a process according to claim 1, wherein said preparation comprises from 0.5 to 25% by weight of a finely divided carotenoid, retinoid or natural colourant having a particle size of less than 0.4 $\mu$m, and does not contain a water-immiscible organic solvent.

* * * * *

UNITED STATES PATENT AND TRADEMARK OFFICE
CERTIFICATE OF CORRECTION

PATENT NO. : 6,406,735 B2
DATED : June 18, 2002
INVENTOR(S) : Hermann Stein et al.

It is certified that error appears in the above-identified patent and that said Letters Patent is hereby corrected as shown below:

Title page,
Item [54], please insert a comma after "CAROTENOID";
Item [57], ABSTRACT,
Line 2, please change "colorant" to -- colourant --;

Column 6,
Line 36, please change "colorants" to -- colourants --;
Line 39, please change "methyltert," to -- methyltert. --.

Signed and Sealed this

Eighteenth Day of February, 2003

JAMES E. ROGAN
*Director of the United States Patent and Trademark Office*